United States Patent
Shimomura

(10) Patent No.: US 8,771,266 B2
(45) Date of Patent: Jul. 8, 2014

(54) ABLATION THERAPEUTIC DEVICE, RESECTOSCOPE AND METHOD OF ABLATING LIVING BODY TISSUE

(75) Inventor: Koji Shimomura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1126 days.

(21) Appl. No.: 12/056,332

(22) Filed: Mar. 27, 2008

(65) Prior Publication Data

US 2009/0043303 A1 Feb. 12, 2009

(30) Foreign Application Priority Data

Mar. 30, 2007 (JP) .................................. 2007-094128

(51) Int. Cl.
*A61B 18/12* (2006.01)

(52) U.S. Cl.
USPC .................... 606/41; 606/45; 606/46; 606/48

(58) Field of Classification Search
USPC ............................................... 606/41, 45–50
See application file for complete search history.

(56) References Cited

U.S. PATENT DOCUMENTS

| | | | | |
|---|---|---|---|---|
| 5,007,907 | A | * | 4/1991 | Nishigaki et al. ............... 606/46 |
| 5,196,011 | A | * | 3/1993 | Korth et al. ....................... 606/46 |
| 5,810,764 | A | * | 9/1998 | Eggers et al. .................... 604/23 |
| 5,919,189 | A | | 7/1999 | Benderev ......................... 606/45 |
| 5,919,191 | A | * | 7/1999 | Lennox et al. ................... 606/48 |
| 5,993,445 | A | | 11/1999 | Issa .................................. 606/46 |
| 6,730,081 | B1 | * | 5/2004 | Desai ............................... 606/40 |
| 2001/0025177 | A1 | * | 9/2001 | Woloszko et al. ............... 606/41 |
| 2004/0019351 | A1 | | 1/2004 | Ohyama et al. .................. 606/46 |
| 2004/0064139 | A1 | * | 4/2004 | Yossepowitch .................. 606/46 |
| 2005/0245927 | A1 | | 11/2005 | Snay et al. ........................ 606/46 |
| 2005/0251134 | A1 | | 11/2005 | Woloszko et al. ............... 606/46 |
| 2005/0267469 | A1 | | 12/2005 | Blocher |
| 2007/0093812 | A1 | * | 4/2007 | Hayashida et al. .............. 606/46 |

FOREIGN PATENT DOCUMENTS

| | | |
|---|---|---|
| GB | 2 362 829 | 12/2001 |
| JP | 5-220172 | 8/1993 |
| JP | 10-43197 | 2/1998 |

(Continued)

OTHER PUBLICATIONS

Untranslated Office Action issued by Japanese Patent Office on May 25, 2010 in connection with corresponding Japanese application No. 2007-094128.

(Continued)

*Primary Examiner* — Michael Peffley
*Assistant Examiner* — Khadijeh Vahdat
(74) *Attorney, Agent, or Firm* — Ostrolenk Faber LLP

(57) ABSTRACT

An ablation therapeutic device includes a therapeutic electrode which is disposed at a distal end portion of a resectoscope and has a first loop-shaped portion at a distal end thereof, and a compression section which has a second loop-shaped portion extending to a position in front of the therapeutic electrode, has a higher rigidity than the therapeutic electrode, and performs an ablation therapeutic treatment of a living body tissue by a push-out operation. The therapeutic electrode has a bend portion which is bent in an obliquely forward direction from a perpendicular plane to a direction of an axis of the resectoscope, and the compression section has a length in a direction of the perpendicular plane, which is less than a length of the bend portion of the therapeutic electrode in the direction of the perpendicular plane.

9 Claims, 9 Drawing Sheets

(56) References Cited

FOREIGN PATENT DOCUMENTS

| | | |
|---|---|---|
| JP | 2001-504000 | 3/2001 |
| WO | WO 98/07377 | 2/1998 |
| WO | WO 2006/117937 | 11/2006 |

OTHER PUBLICATIONS

English translation of Japanese Office Action issued May 25, 2010 in connection with corresponding Japanese application 2007-094128.
Extended European Search Report for corresponding European Application No. 08005781.3-2305 dated Aug. 4, 2008.

* cited by examiner

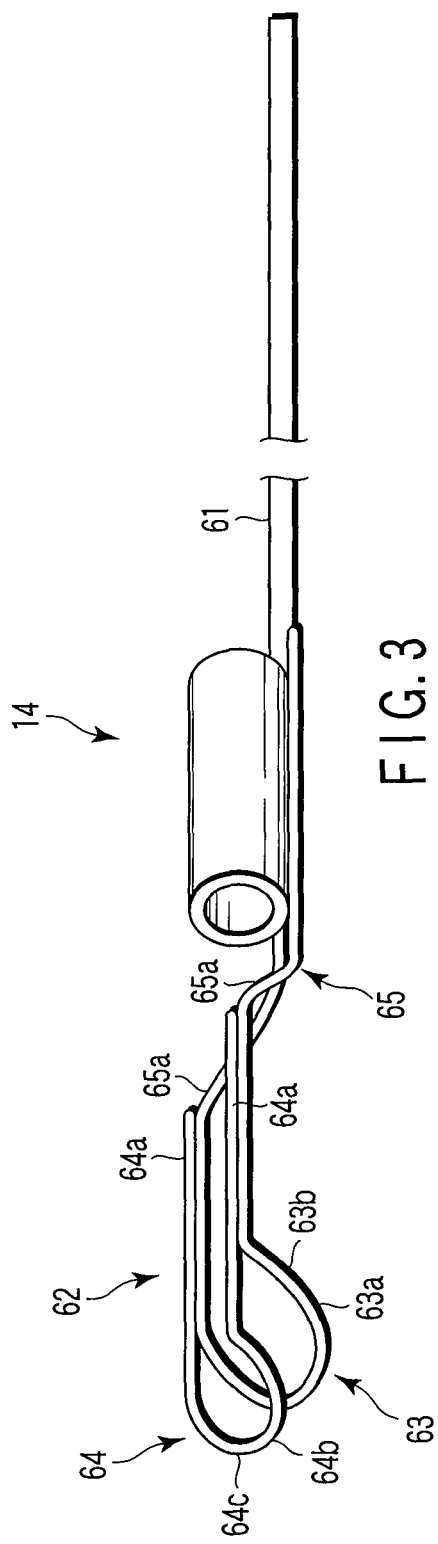
FIG. 3
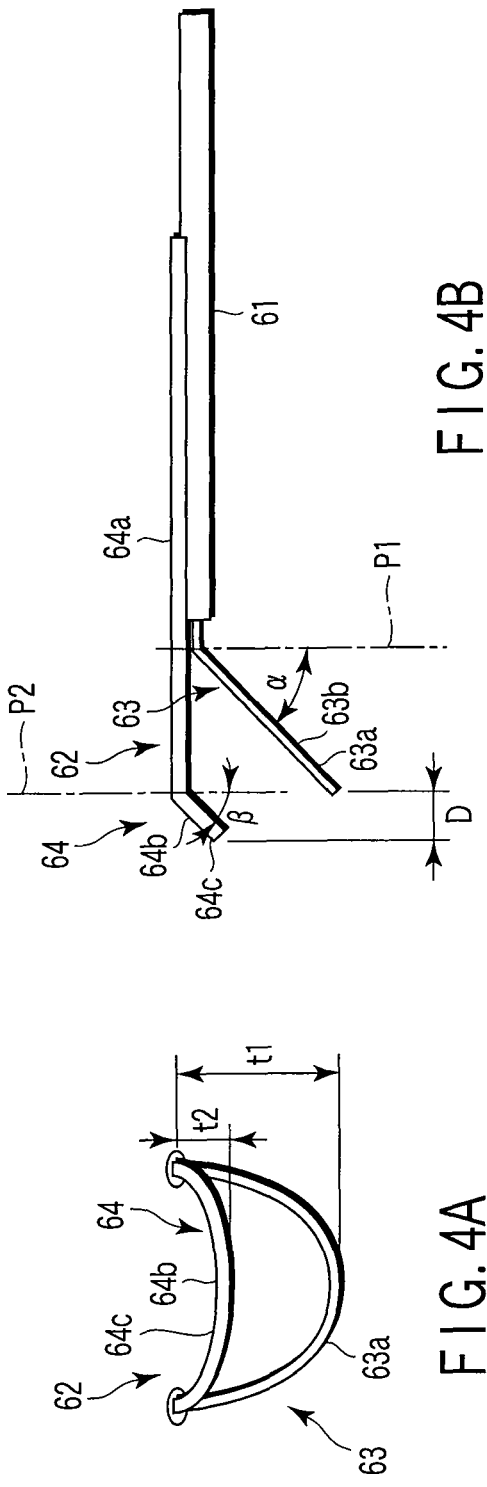
FIG. 4A
FIG. 4B

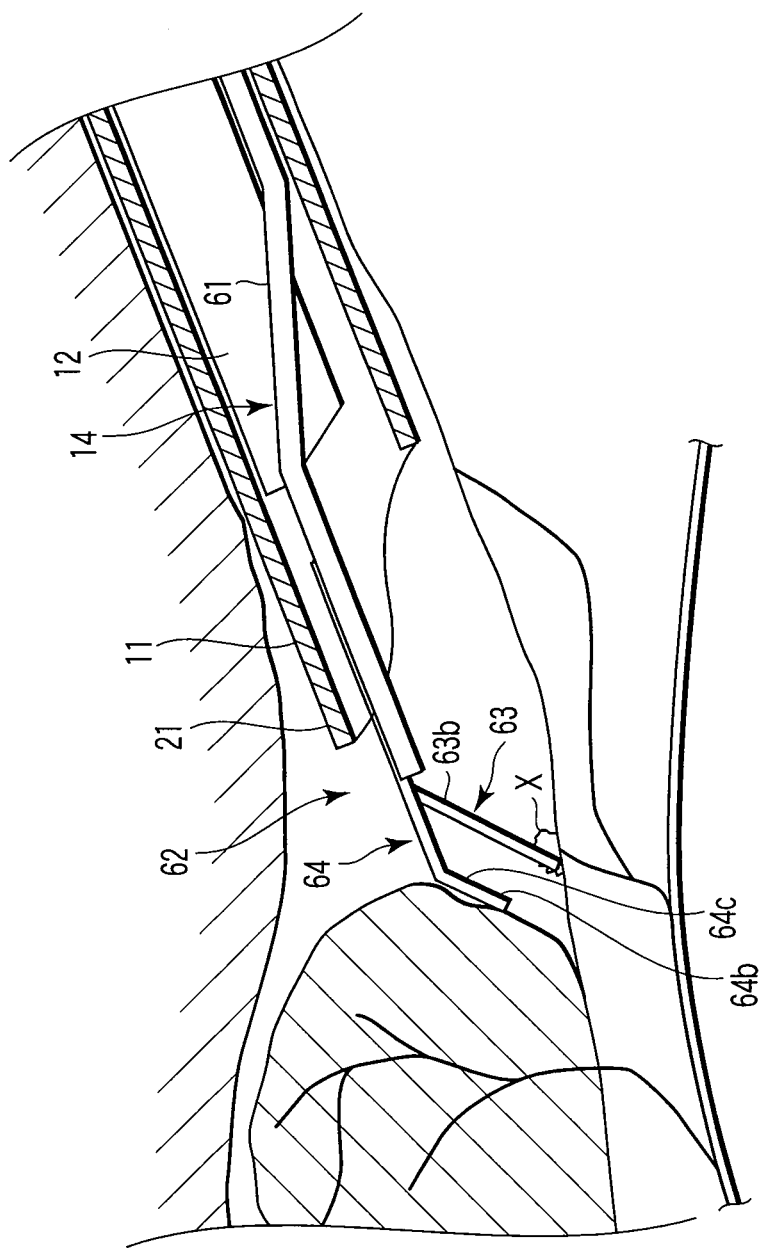
F I G. 7

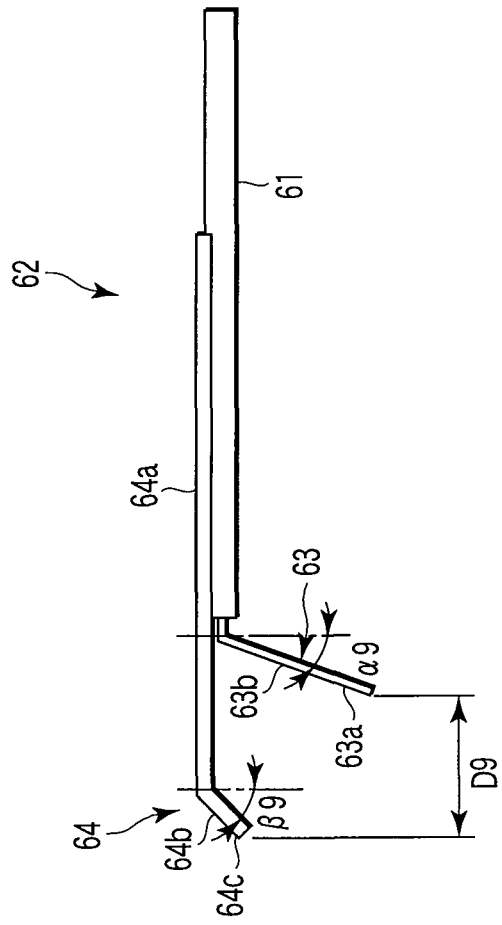
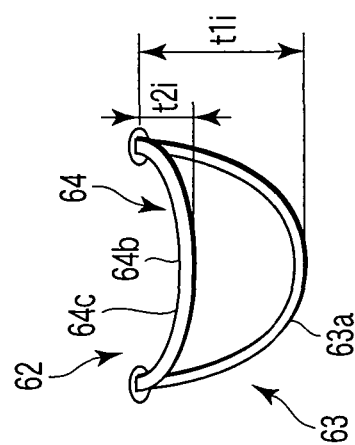
FIG. 10B
FIG. 10A

ABLATION THERAPEUTIC DEVICE, RESECTOSCOPE AND METHOD OF ABLATING LIVING BODY TISSUE

CROSS-REFERENCE TO RELATED APPLICATIONS

This application is based upon and claims the benefit of priority from prior Japanese Patent Application No. 2007-094128, filed Mar. 30, 2007, the entire contents of which are incorporated herein by reference.

BACKGROUND OF THE INVENTION

1. Field of the Invention

The present invention relates to a therapeutic device which performs vaporization, incision, resection, enucleation of a living tissue, such as the prostate, by means of electrical resection under observation by an endoscope, and to a resectoscope and a method of ablating a living body tissue.

2. Description of the Related Art

In general, a resectoscope is used for transurethral resection (TUR) and transcervical resection (TCR). This apparatus mainly includes an elongated hollow outer sheath, an optical scope (also referred to as "scope") which is an endoscope for observation, and an electrode unit for resecting a living body tissue. The outer sheath is inserted in a body cavity. The optical scope and the electrode unit are inserted in the outer sheath.

Jpn. Pat. Appln. KOKAI Publication No. 5-220172 (Patent Document 1) shows an example of a resection electrode of a medical resectoscope for use in, e.g. excision of the prostate. In this apparatus, the resection electrode is projectably/retractably provided in a hollow shaft of the resectoscope. The resection electrode includes a pair of long rods, and a resection loop. The resection loop is bent in a semi-circular shape in the state in which the resection loop is bent at about 90° between the distal end portions of the paired rods. Further, a spacer is attached in front of the resection loop. The spacer restricts the depth of resection of the resection loop.

When the apparatus of Patent Document 1 is used, a high-frequency power is turned on. Then, the resection electrode is projected from the hollow shaft of the resectoscope. In this state, the resection electrode is moved back and forth, and thereby the prostate is resected. At this time, the resection electrode is pulled toward the near side. Thus, the prostate is resected by the resection loop.

At the time of the operation of resecting a piece of tissue by pulling the resection loop, the spacer is kept in contact with the surface of the tissue. As a result, the depth of resection of the resection loop is automatically restricted, and the resection loop is prevented from advancing to a depth that is greater than the depth restricted by the spacer.

BRIEF SUMMARY OF THE INVENTION

According to an aspect of the present invention, there is provided an ablation therapeutic device in which a main body of the ablation therapeutic device, which has an ablation therapeutic treatment section at a distal end thereof, and an endoscope are inserted in an outer sheath, and an operation section having a handle section, which reciprocally moves the ablation therapeutic treatment section in an axial direction of the outer sheath, is provided at a proximal end portion of the outer sheath, wherein the ablation therapeutic device comprises: a therapeutic electrode which is disposed at a distal end portion of the main body of the ablation therapeutic device, and has a first loop-shaped portion at a distal end thereof; and a compression section which has a second loop-shaped portion extending to a position in front of the therapeutic electrode, has a higher rigidity than the therapeutic electrode, and performs an ablation therapeutic treatment of a living body tissue by a push-out operation, that the therapeutic electrode has a bend portion which is bent in an obliquely forward direction from a perpendicular plane to a direction of an axis of the main body of the ablation therapeutic device, and that the compression section has a length in a direction of the perpendicular plane, which is less than a length of the bend portion of the therapeutic electrode in the direction of the perpendicular plane.

In the above structure, when therapeutic treatment, such as enucleation of the prostate, is performed, the first loop-shaped portion at the distal end of the therapeutic electrode is pressed on the living body tissue, and thus incision/coagulation of the living body tissue is performed. Further, the second loop-shaped portion of the compression section, which has a higher rigidity than the therapeutic electrode, is pushed out while being in pressure contact with the living body tissue, and thereby the living body tissue is ablated. In this case, the second loop-shaped portion of the compression section is extended to the position in front of the therapeutic electrode. Thereby, the operation of ablating the living body tissue by the compression section is not hindered by the bend portion of the therapeutic electrode. Further, the therapeutic electrode has the bend portion which is bent in an obliquely forward direction from the perpendicular plane to the direction of the axis of the main body of the ablation therapeutic device. The length of the compression section in the direction of the perpendicular plane is set to be less than the length of the bend portion of the therapeutic electrode. Thereby, when bleeding occurs at the time of ablating the living body tissue by the compression section, the bleeding can be stopped by pressing the first loop-shaped portion at the distal end of the therapeutic electrode on the living body tissue.

Preferably, the main body of the ablation therapeutic device comprises an elongated insertion section which is inserted in a body cavity; the ablation therapeutic treatment section disposed at a distal end portion of the insertion section; and the operation section which is provided at a proximal end portion of the insertion section and has the handle section which reciprocally moves the ablation therapeutic treatment section in an axial direction of the insertion section, and the ablation therapeutic treatment section includes the therapeutic electrode and the compression section.

In the above structure, when the main body of the ablation therapeutic device is used, the ablation therapeutic treatment section is reciprocally moved in the axial direction of the insertion section by the operation of the handle section by the operation section. At this time, the first loop-shaped portion at the distal end of the therapeutic electrode is pressed on the living body tissue, and thus incision/coagulation of the living body tissue is performed. Further, the second loop-shaped portion of the compression section, which has a higher rigidity than the therapeutic electrode, is pushed out while being in pressure contact with the living body tissue, and thereby the living body tissue is ablated.

Preferably, the ablation therapeutic treatment section includes the therapeutic electrode and a return electrode which is formed of a metallic portion of the outer sheath or the like, the ablation therapeutic treatment section being composed of a bipolar-type high-frequency therapeutic device which is supplied with a high-frequency current between the therapeutic electrode and the return electrode.

In the above structure, high-frequency therapeutic treatment by the therapeutic electrode of the ablation therapeutic treatment section is performed by the bipolar-type high-frequency therapeutic device which is supplied with a high-frequency current between the therapeutic electrode and the return electrode that is formed of the metallic portion of the outer sheath or the like.

Preferably, the compression section is formed of a large-diameter wire having a wire diameter that is greater than a wire diameter of the therapeutic electrode.

In the above structure, the compression section is formed of a large-diameter wire having a wire diameter that is greater than a wire diameter of the therapeutic electrode. Thereby, the rigidity of the compression section is increased, and the compression section is made less bendable when the living body tissue is ablated by the push-out operation of the compression section.

Preferably, the compression section includes a coating provided on the wire and formed of Teflon or the like.

In the above structure, the coating provided for the compression section enables smooth ablation of a living tissue without invasion of that living tissue.

Preferably, the compression section has a second bend portion which is bent in an obliquely forward direction from a perpendicular plane to the direction of the axis of the main body of the ablation therapeutic device, and a bend angle $\beta$ of the second bend portion is substantially equal to a bend angle $\alpha$ of the bend portion of the therapeutic electrode.

In the above structure, the living body tissue is ablated by the ablation therapeutic treatment section in which the bend angle $\beta$ of the second bend portion of the compression section is substantially equal to the bend angle $\alpha$ of the bend portion of the therapeutic electrode.

Preferably, the bend angle $\beta$ of the second bend portion is different from the bend angle $\alpha$ of the bend portion of the therapeutic electrode.

In the above structure, the living body tissue is ablated by the ablation therapeutic treatment section in which the bend angle $\beta$ of the second bend portion of the compression section is different from the bend angle $\alpha$ of the bend portion of the therapeutic electrode.

According to another aspect of the invention, there is provided a resectoscope in which an ablation therapeutic treatment section, which performs an ablation therapeutic treatment of a living body tissue, and an endoscope are inserted in an outer sheath, and an operation section having a handle section, which reciprocally moves the ablation therapeutic treatment section in an axial direction of the outer sheath, is provided at a proximal end portion of the outer sheath, wherein the ablation therapeutic treatment section comprises: a therapeutic electrode having a first loop-shaped portion at a distal end thereof; and a compression section which has a second loop-shaped portion extending to a position in front of the therapeutic electrode, has a higher rigidity than the therapeutic electrode, and performs an ablation therapeutic treatment of a living body tissue by a push-out operation, that the therapeutic electrode has a bend portion which is bent in an obliquely forward direction from a perpendicular plane to a direction of an axis of the ablation therapeutic treatment section, and that the compression section has a length in a direction of the perpendicular plane, which is less than a length of the bend portion of the therapeutic electrode in the direction of the perpendicular plane.

In the above structure, within the visual field of observation by the endoscope of the resectoscope, the first loop-shaped portion at the distal end of the therapeutic electrode is pressed on the living body tissue, and thus incision/coagulation of the living body tissue is performed. Further, the second loop-shaped portion of the compression section, which has a higher rigidity than the therapeutic electrode, is pushed out while being in pressure contact with the living body tissue, and thereby the living body tissue is ablated. In this case, the second loop-shaped portion of the compression section is extended to the position in front of the therapeutic electrode. Thereby, the operation of ablating the living body tissue by the compression section is not hindered by the bend portion of the therapeutic electrode. Further, the therapeutic electrode has the bend portion which is bent in an obliquely forward direction from the perpendicular plane to the direction of the axis of the main body of the ablation therapeutic device. The length of the compression section in the direction of the perpendicular plane is set to be less than the length of the bend portion of the therapeutic electrode. Thereby, when bleeding occurs at the time of ablating the living body tissue by the compression section, the bleeding can be stopped by pressing the first loop-shaped portion at the distal end of the therapeutic electrode on the living body tissue.

According to still another aspect of the invention, there is provided a method of ablating a living body tissue, comprising: a high-frequency therapeutic treatment step of performing a high-frequency therapeutic treatment of the living body tissue by pressing the therapeutic electrode on the living body tissue in a state in which a high-frequency current is supplied to the therapeutic electrode having a first loop-shaped portion which is disposed at a distal end portion of a main body of an ablation therapeutic device; and an ablation operation step of performing an ablation operation of the living body tissue by a compression section by pressing the compression section on the living body tissue, the compression section having a second loop-shaped portion which extends to a position in front of the therapeutic electrode and has a higher rigidity than the therapeutic electrode.

In this method, a high-frequency therapeutic treatment of the living body tissue is performed by pressing the first loop-shaped portion of the therapeutic electrode on the living body tissue in the state in which a high-frequency current is supplied to the therapeutic electrode which is disposed at a distal end portion of a main body of an ablation therapeutic device (high-frequency therapeutic treatment step). Then, an ablation operation of the living body tissue is performed by a compression section by pressing a second loop-shaped portion of the compression section on the living body tissue, the compression section extending to a position in front of the therapeutic electrode and having a higher rigidity than the therapeutic electrode (ablation operation step). Further, where necessary, the ablation operation step and the high-frequency therapeutic treatment step are alternately repeated, and the ablation operation of the living body tissue is progressed.

According to the present invention, it is possible to provide a therapeutic device for ablation, which has a high durability for use in ablation of the prostate and can efficiently perform therapeutic treatments including incision and coagulation, and also to provide a resectoscope and a method of ablating a living body tissue.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL
VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 schematically shows the structure of the entire system of a resectoscope according to a first embodiment of the present invention;

FIG. 3 is a perspective view of an ablation therapeutic treatment section of the resectoscope according to the first embodiment;

FIG. 4A is a front view of the ablation therapeutic treatment section of the resectoscope according to the first embodiment;

FIG. 4B is a side view of the ablation therapeutic treatment section;

FIG. 7 is a longitudinal cross-sectional view showing the state of use of the resectoscope according to the first embodiment;

FIG. 10A is a front view showing a ninth modification of the ablation therapeutic treatment of the resectoscope according to the first embodiment; and FIG. 10B is a side view showing the ablation therapeutic treatment according to the ninth modification.

DETAILED DESCRIPTION OF THE INVENTION

Figure 1:
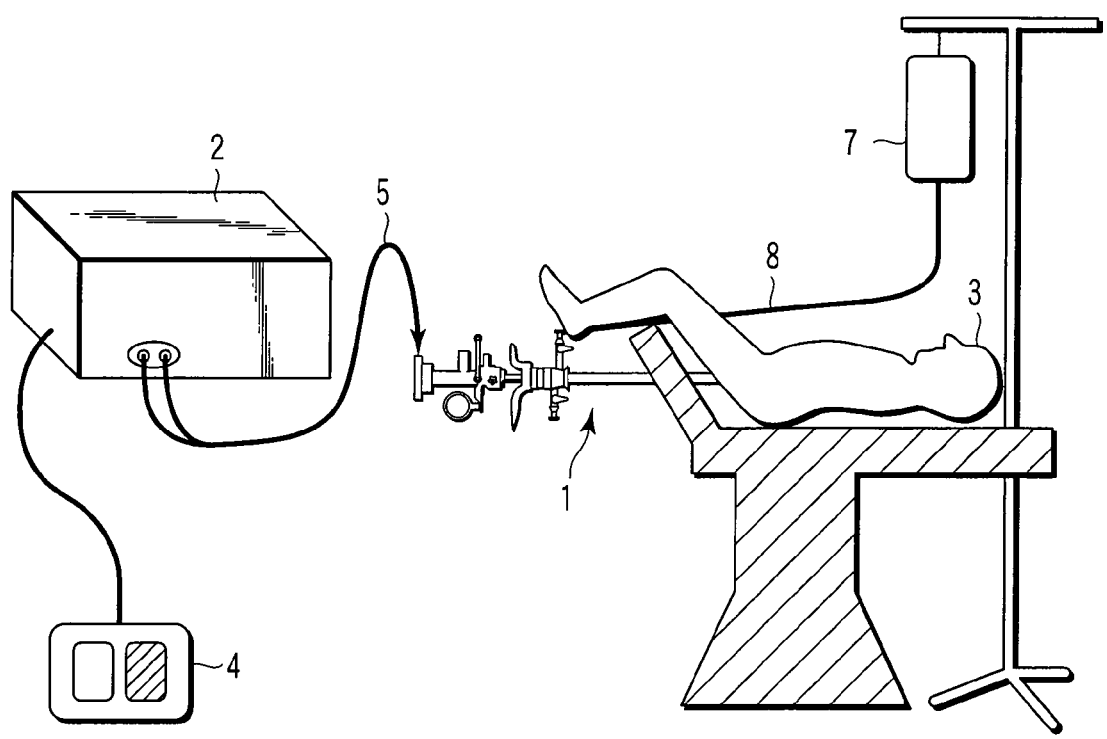

A first embodiment of the present invention will now be described with reference to FIG. 1 to FIG. 7. FIG. 1 schematically shows the structure of the entire system of a resectoscope apparatus according to the present embodiment. FIG. 1 shows the state in which transurethral resection is performed by using the resectoscope apparatus. The resectoscope apparatus comprises a resectoscope (main body of an ablation therapeutic device) 1 and a high-frequency power supply device 2. A foot switch 4 is connected to the high-frequency power supply device 2.

The high-frequency power supply device 2 is connected to the resectoscope 1. The high-frequency power supply device 2 performs supply of a high-frequency cauterization current (hereinafter referred to as "active current") to a therapeutic electrode 63 of an electrode unit 14 (see FIG. 3) to be described later, and recovery of feedback current (hereinafter referred to as "return current").

Figure 2:
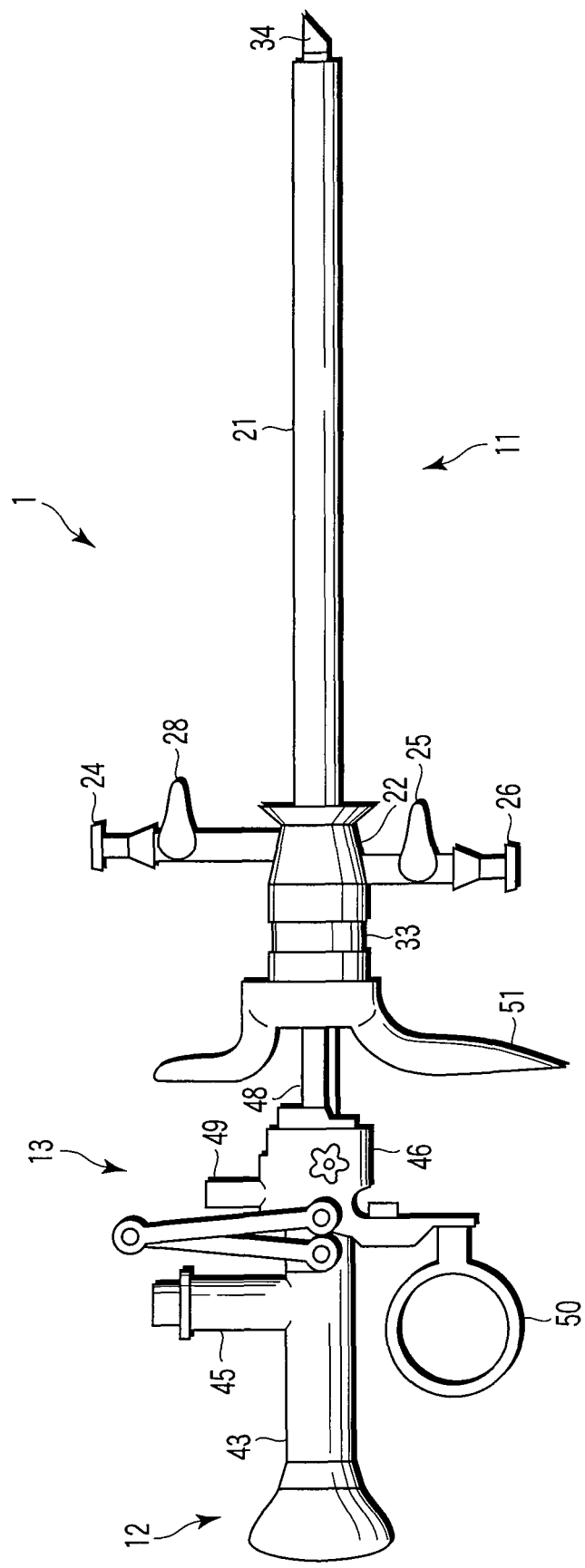
FIG. 2 is a side view of the resectoscope according to the first embodiment.

As shown in FIG. 2, the resectoscope 1 includes a hollow outer sheath 11, a scope 12, a handle section 13 and the electrode unit 14. The outer sheath 11 is an outer sheath tube having a through-hole (tube cavity). The scope 12 is an optical scope (endoscope) which is disposed in the through-hole in the outer-sheath 11. The handle section 13 is an operation section. The electrode unit 14 is an active electrode which is disposed in the through-hole of the outer sheath 11.

Figure 5:
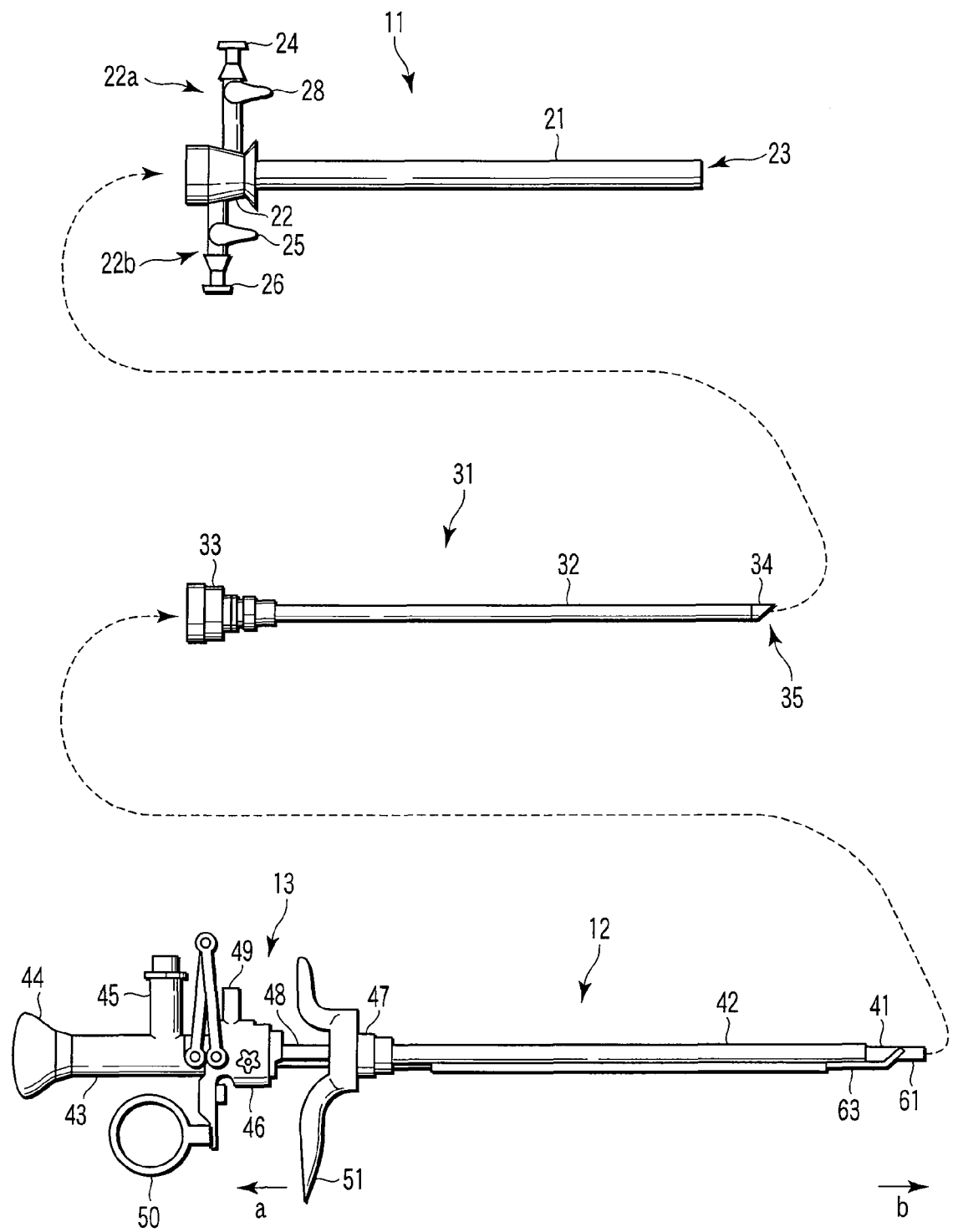
FIG. 5 is a view for describing an assembly work of the resectoscope according to the first embodiment.

As shown in FIG. 5, the outer sheath 11 includes a hollow insertion section 21 and a proximal main body section 22. The insertion section 21 is inserted into a body cavity through, for example, the urethra. The proximal main body section 22 is provided at the rear end of the insertion section 21.

A distal end portion of the insertion section 21 has an opening section 23. Two fluid conduits 22a and 22b are provided on a side peripheral portion of the proximal main body section 22. One fluid conduit 22a is a conduit for feeding, e.g. physiologic saline, which has electrical conductivity to the therapeutic section as perfusate. The fluid conduit 22b is a conduit for draining, e.g. physiologic saline. The fluid conduit 22a for liquid feed has a liquid feed mouthpiece 24 that is a tube connection means, and a cock 28. The liquid conduit 22b for drainage similarly has a liquid drainage mouthpiece 26 that is a tube connection means, and a cock 25.

A tube for feeding a liquid is connected to the liquid feed mouthpiece 24. A tube for draining a liquid is connected to the liquid drainage mouthpiece 26. The liquid feed and liquid drainage can be controlled by operating the cocks 28 and 25.

An inner sheath 31 is inserted in the outer sheath 11. The inner sheath 31 comprises a hollow insertion section 32, a proximal main body section 33 and a distal end portion 34. The insertion section 32 is inserted into the outer sheath 11 from a rear-side opening of the proximal main body section 22 of the outer sheath 11, and is disposed in the insertion section 21. The proximal main body section 33 is provided at the rear end of the insertion section 32. The distal end portion 34 is provided at the distal end of the insertion section 32, and is formed of, e.g. a hard resin member which is an insulating member. The distal end of the distal end portion 34 has an opening portion 35.

The scope 12, together with the electrode unit 14, is inserted from a rear-side opening of the proximal main body section 33 of the inner sheath 31, and is disposed in the inner sheath 31. There may be a case in which the scope 12 is used in the state in which only the inner sheath 31 is attached, without using the outer sheath 11.

The scope 12 comprises a hard insertion tube 41, a guide tube 42 and a proximal section 43. The insertion tube 41 is formed of, e.g. metal material in an elongated straight tube shape. An observation optical system is built in the insertion tube 41. The insertion tube 41 is inserted and disposed in the inner sheath 31. The insertion tube 41 is passed through the guide tube 42. The proximal section 43 is provided at a proximal end portion of the guide tube 42.

An eyepiece section 44 for visual observation by a surgeon is provided at the proximal end of the proximal section 43. A light guide connection portion 45 is provided on a side portion of the proximal section 43. A light guide (not shown) for supplying illumination light for observation to a region of observation is connected to the light guide connection portion 45.

As shown in FIG. 3, the electrode unit 14 includes an elongated metal pipe 61 and an ablation therapeutic treatment section 62. An insulation tube (not shown) is coated on the outer periphery of the metal pipe 61. A proximal end portion of the metal pipe 61 is exposed from the rear end of the insulation tube, and an electrode connection section is formed at the proximal end portion of the metal pipe 61.

The ablation therapeutic treatment section 62 includes a therapeutic electrode 63 and a compression section 64. A proximal end portion of a parallel lead member 65 is coupled to a distal end portion of the metal pipe 61. The parallel lead member 65 is a two-forked member having two substantially parallel straight wire portions 65a, which extend in the direction of the axis of insertion of the scope 12.

The therapeutic electrode 63 is an elongated wire-shaped electrode. The therapeutic electrode 63 includes a first loop-shaped portion 63a having, for example, an arcuate shape. Both end portions of the therapeutic electrode 63 are connected to distal end portions of the two straight wire portions 65a of the parallel lead member 65. Further, the therapeutic electrode 63 includes a bend portion 63b which is bent at a bend angle $\alpha$, as shown in FIG. 4B, in an obliquely forward direction from a perpendicular plane P1 to the direction of the axis of insertion of the scope 12 (i.e. the axial direction of the main body of the ablation therapeutic device). In the present embodiment, the bend angle $\alpha$ of the bend portion 63b of the therapeutic electrode 63 is set at, e.g. 45°. In addition, the length t1 of the bend portion 63b of the therapeutic electrode 63 in the direction of the perpendicular plane P1 is set at an arbitrary length.

The compression section 64 includes a second loop-shaped portion 64b between two substantially parallel straight wire portions 64a, which extend in the direction of the axis of insertion of the scope 12. The compression section 64 is formed of a wire having a greater wire diameter than the wire diameter of the therapeutic electrode 63. Thereby, the rigidity of the compression section 64 is set to be higher than that of the therapeutic electrode 63.

As shown in FIG. 4B, the compression section 64 is extended forward by a distance D from the therapeutic electrode 63. Further, the compression section 64 includes a bend portion 64c which is bent at a bend angle $\beta$ in an obliquely forward direction from a perpendicular plane P2 to the direction of the axis of insertion of the scope 12 (i.e. the axial direction of the main body of the ablation therapeutic device). In the present embodiment, the bend angle $\beta$ of the bend portion 64c of the compression section 64 is set at the same angle (45°) as the bend angle $\alpha$ of the bend portion 63b of the therapeutic electrode 63. Further, as shown in FIG. 4A, the length t2 of the bend portion 64c of the compression section 64 in the direction of the perpendicular plane P2 is set to be less than the length t1 of the bend portion 63b of the therapeutic electrode 63.

The electrode unit 14 is disposed in the inner sheath 31 such that the therapeutic electrode 63 is advancible/retractable in the direction of insertion of the inner sheath 31 in the opening 35 of the distal end portion 34 of the inner sheath 31. A proximal end portion of the metal pipe 61 extends from the proximal end surface of the proximal main body section 33 through the insertion section 32 and proximal main body section 33 of the inner sheath 31, and is fixed to a slider 46 (to be described later).

The handle section 13 mainly comprises a sheath connection section 47, a guide tube 48 and a substantially pipe-shaped slider 46. The sheath connection section 47 is detachably connected to the proximal main body section 33. The guide tube 48 is projected rearward from the rear end surface of the sheath connection section 47. The insertion tube 41 is inserted in the sheath connection section 47. The slider 46 is held on the guide tube 48 so as to be slidable in the direction of the axis of insertion of the scope 12.

The slider 46 is provided with an electrode fixing section (not shown), a high-frequency power supply connector 49, and an annular thumb ring 50. The electrode fixing section is an electrical connection section for connection to the electrode connection section of the rear end portion of the electrode unit 14. A power cable 5 extending from the high-frequency power supply device 2 is detachably connected to the high-frequency power supply connector 49. The thumb ring 50 is a finger receiving section in which the thumb of the surgeon is hooked.

The slider 46 and the sheath connection section 47 are coupled in the state in which the slider 46 and sheath connection section 47 are urged in a direction away from each other by a resilient member (not shown) such as a spring. Specifically, the slider 46 is always urged toward the eyepiece section 44 by the resilient member. In the state in which no force is applied to a finger hook section 51 and the ring 50, the distal end portion of the ablation therapeutic treatment section 62 and the distal end portion of the insertion tube 41 are set to be disposed at substantially the same position in the direction of insertion of the scope 12.

While holding by the hand the finger hook section 51 of the sheath connection section 47 and the thumb hook ring 50 of the slider 46, the surgeon performs a proper operation so as to decrease the distance between the finger hook section 51 and ring 50. Thereby, the slider 46 moves toward the distal end of the scope 12, relative to the guide tube 48. Thus, the ablation therapeutic treatment section 62 of the electrode unit 14 moves so as to project from the distal end of the insertion tube 41.

The high-frequency power supply connector 49 and the above-described electrode fixing section are electrically connected by, e.g. a lead wire. Thus, by connecting the cable 5, which extends from the high-frequency power supply device 2, to the high-frequency power supply connector 49, power is supplied to the therapeutic electrode 63 of the electrode unit 14, and therapeutic treatment of a diseased part can be performed. In the present embodiment, a return electrode of the bipolar-type high-frequency therapeutic device is formed of a metallic part, such as the insertion section 21 of the outer sheath 11.

Figure 6:
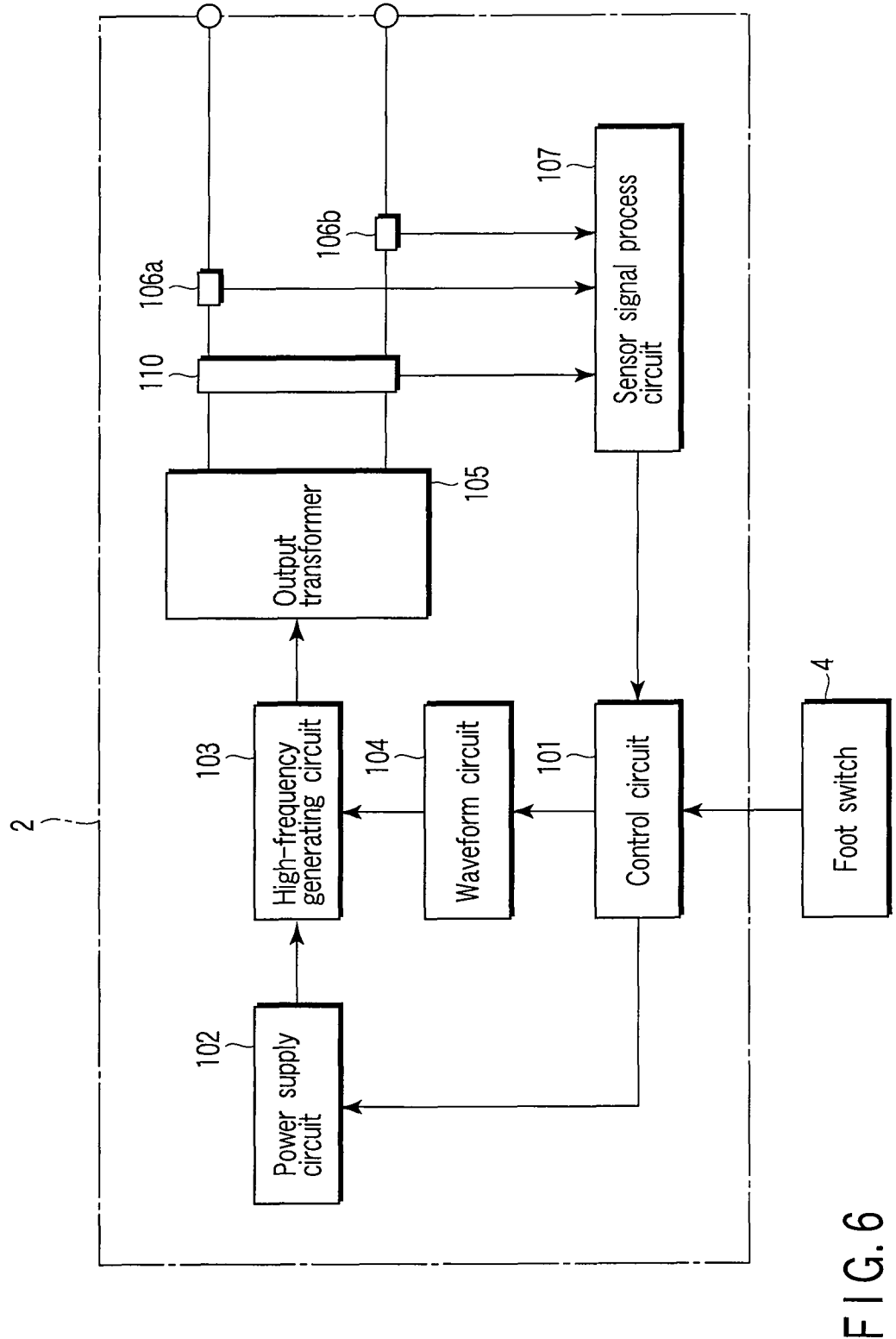
FIG. 6 is a block diagram showing the structure of a high-frequency power device of the resectoscope according to the first embodiment.

FIG. 6 is a block diagram showing the structure of the high-frequency power supply device 2 of the resectoscope 1 according to the present embodiment. As shown in FIG. 6, the high-frequency power supply device 2 includes a control circuit 101, a power supply circuit 102, a high-frequency generating circuit 103, a waveform circuit 104, an output transformer circuit 105, a voltage sensor 110, two current sensors 106a and 106b, and a sensor signal process circuit 107. The control circuit 101 receives a signal from the foot switch 4 and executes control of power supply. The power supply circuit 102 is controlled by the control circuit 101 and generates DC power. The high-frequency generating circuit 103 switches the DC power from the power supply circuit 102 and generates high-frequency power. The waveform circuit 104 is controlled by the control circuit 101 and supplies to the high frequency generating circuit 103 a waveform signal of high-frequency power that is generated by the high-frequency generating circuit 103. The output transformer circuit 105 amplifies the high-frequency voltage of the high-frequency power that is generated by the high frequency generating circuit 103 and applies the amplified voltage between a terminal for the therapeutic electrode 63 and a terminal for return current, thus supplying a high-frequency current to the therapeutic electrode 63. The voltage sensor 110 detects the voltage of the high-frequency output from the output transformer circuit 105. The current sensors 106a and 106b detects the high-frequency current that is output from the output transformer circuit 105. The sensor signal process circuit 107

A/D converts the voltage value detected by the voltage sensor 110 and the current value detected by the current sensors 106a and 106b.

The control circuit 101 calculates an impedance of a living body tissue on the basis of digitized voltage data and current data from the sensor signal process circuit 107, and controls the power supply circuit 102 and waveform circuit 104.

Next, the operation of the above-described structure is described. When the resectoscope apparatus of this embodiment is used, the distal end portion of the resectoscope 1 is inserted transurethrally into a subject 3, as shown in FIG. 1. The control of power supply from the high-frequency power supply device 2 to the therapeutic electrode 63 is executed by turn on/off of the foot switch 4 that is connected to the high-frequency power supply device 2.

In addition, in FIG. 1, in the resectoscope 1, physiologic saline with electrical conductivity is supplied as perfusate into a body cavity, such as the bladder, from a physiologic saline pack 7 via a sterilized tube 8. After filling the body cavity with physiologic saline, the surgeon inserts the resectoscope 1 into the body cavity and moves the ablation therapeutic treatment section 62 of the electrode unit 14 to the surface of a body tissue, which undergoes incision, resection, etc., while viewing an image of the endoscope for observation. Then, by turning on the foot switch 4, incision, etc. is performed.

In addition, as shown in FIG. 7, when transurethral resection is performed by the resectoscope 1 of this embodiment, the ablation therapeutic treatment section 62 of the electrode unit 14 is set in such a state as to project from the distal end of the resectoscope 1. In this state, if the foot switch 4 is turned on, a high-frequency current is supplied from the high-frequency power supply device 2 via the cable 5 to the therapeutic electrode 63 of the resectoscope 1. Further, the high-frequency current, which is output from the therapeutic electrode 63, is recovered, as return current, to the high-frequency power supply device 2 via the living body tissue, physiologic saline and outer sheath 11. At this time, a high-frequency current is supplied between the therapeutic electrode 63 of the ablation therapeutic treatment section 62 and the return electrode, and bipolar-type high-frequency therapeutic treatment (incision, resection, transpiration, coagulation, etc. of a living body tissue) is performed by the therapeutic electrode 63 of the ablation therapeutic treatment section 62.

In the resectoscope 1 of this embodiment, in the state in which the high-frequency current is supplied to the therapeutic electrode 63 having the first loop-shaped portion 63a, the ablation therapeutic treatment section 62 performs a high-frequency therapeutic treatment step for subjecting a living body tissue to high-frequency therapeutic treatment, with the therapeutic electrode 63 being pressed on the living body tissue. Further, the compression section 64, which is extended to the position in front of the therapeutic electrode 63 and has the second loop-shaped portion 64b having a higher rigidity than the treatment electrode 63, is pressed on the living body tissue, and the compression section 64 performs an ablation operation step for ablating the living body tissue. Specifically, when the prostate is ablated, as shown in FIG. 7, the therapeutic electrode 63 is pressed on the living body tissue, and a part of the prostate is incised. Then, the compression section 64 is pressed on the incised part, and the prostate ablation operation is progressed by the operation of pushing out the compression section 64. If bleeding occurs during the prostate ablation operation, the therapeutic electrode 63 is pressed on a bleeding part X, and the bleeding is stopped by coagulation by high-frequency therapeutic treatment.

The embodiment with the above-described structure has the following advantageous effects. Specifically, in the resectoscope 1 of this embodiment, the ablation therapeutic treatment section 62 is provided with the therapeutic electrode 63 and compression section 64. The therapeutic electrode 63 has the first loop-shaped portion 63a at its distal end. The compression section 64 has the second loop-shaped portion 64b which is extended to the position in front of the therapeutic electrode 63, has a higher rigidity than the therapeutic electrode 63, and performs the ablation therapeutic treatment of the living body tissue by the push-out operation. The therapeutic electrode 63 has the bend portion 63b which is bent in an obliquely forward direction from the perpendicular plane P1 to the direction of the axis of the resectoscope 1. The length of the compression section 64 in the direction of the perpendicular plane P2 is set to be less than the length of the bend portion 63b of the therapeutic electrode 63. Thereby, when therapeutic treatment, such as ablation of the prostate, is performed, the first loop-shaped portion 63a at the distal end of the therapeutic electrode 63 is pressed on the living body tissue, and thus incision/coagulation of the living body tissue is performed. Further, the second loop-shaped portion 64b of the compression section 64, which has a higher rigidity than the therapeutic electrode 63, is pushed out while being in contact with the living body tissue, and thereby the living body tissue is ablated. In this case, the second loop-shaped portion 64b of the compression section 64 is extended to the position in front of the therapeutic electrode 63. Thereby, the operation of ablating the living body tissue by the compression section 64 is not hindered by the bend portion 63b of the therapeutic electrode 63, and this operation can be facilitated.

Further, the therapeutic electrode 63 has the bend portion 63b which is bent in an obliquely forward direction from the perpendicular plane P1 to the direction of the axis of the resectoscope 1. The length of the compression section 64 in the direction of the perpendicular plane P2 is set to be less than the length of the bend portion 63b of the therapeutic electrode 63. Thereby, when bleeding occurs at the time of ablating the living body tissue by the compression section 64, the compression section 64 does not hinder the homeostasis operation for stopping bleeding by pressing the first loop-shaped portion 63a at the distal end of the therapeutic electrode 63 on the living body tissue, and the homeostasis operation can be facilitated.

Moreover, the second loop-shaped portion 64b of the compression section 64, which has a higher rigidity than the therapeutic electrode 63, is pushed out while being in contact with the living body tissue, and thereby therapeutic treatment, such as ablation of the living body tissue, is performed. Thus, no bending of the therapeutic electrode 63 occurs, unlike the case in which therapeutic treatment, such as ablation of the living body tissue, is performed in the state in which the therapeutic electrode 63 is put in contact with the living body tissue. Therefore, compared to the prior art, the durability of the therapeutic electrode 63 can be increased. Thus, the durability of the ablation therapeutic treatment section 62 of the resectoscope 1 of this embodiment can be increased when the ablation therapeutic treatment section 62 is used for ablation of the prostate, incision/resection can also be performed, and therapeutic treatment can efficiently be performed.

Figure 8:
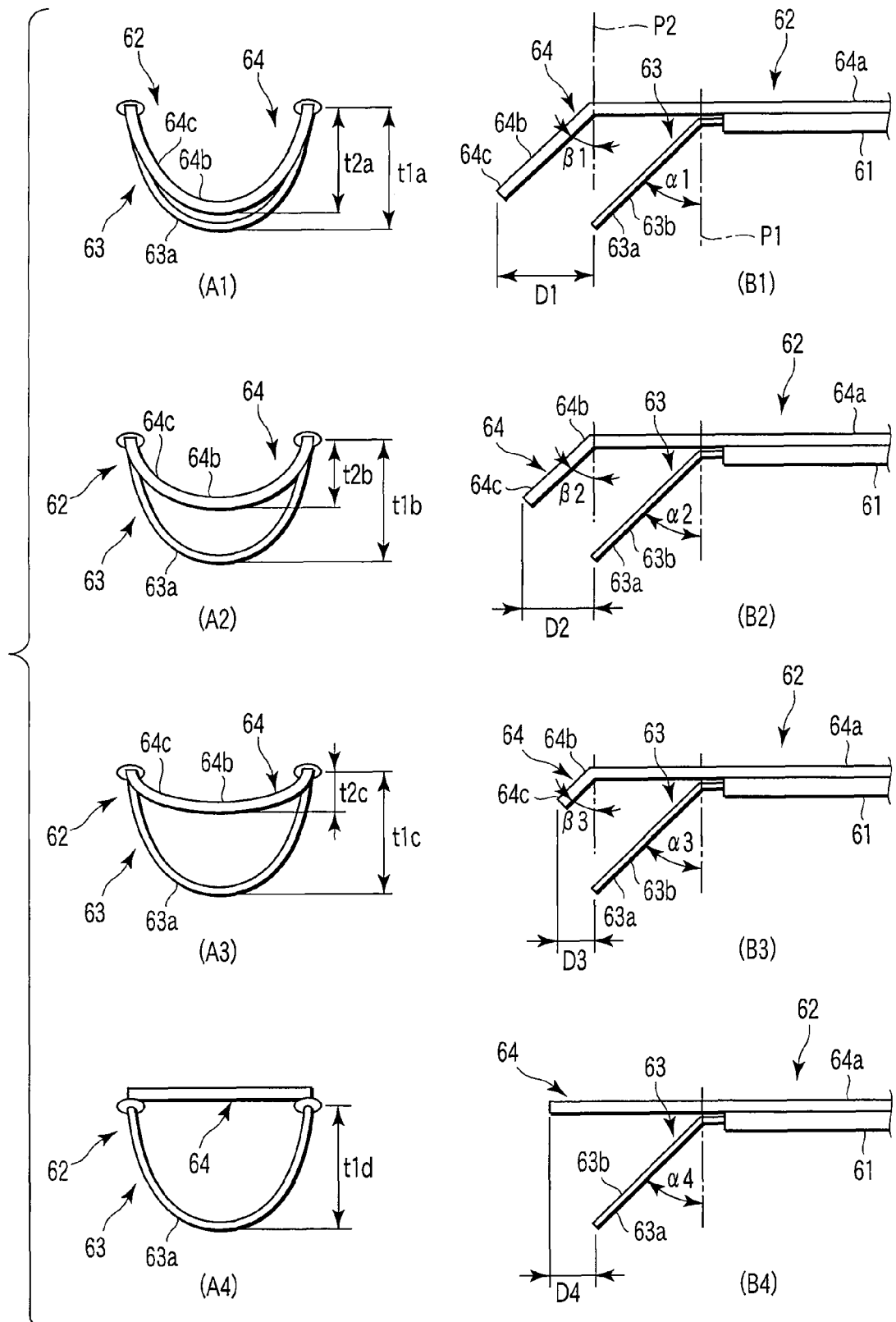
FIG. 8 shows first to fourth modifications of the ablation therapeutic treatment section of the resectoscope according to the first embodiment.

The ablation therapeutic treatment section 62 of the resectoscope 1 of the first embodiment can be modified as follows. Parts (A1) and (B1) of FIG. 8 show a first modification of the ablation therapeutic treatment section 62 of the resectoscope 1 of the first embodiment. Parts (A2) and (B2) of FIG. 8 show a second modification of the ablation therapeutic treatment section 62. Parts (A3) and (B3) of FIG. 8 show a third modification of the ablation therapeutic treatment section 62. Parts (A4) and (B4) of FIG. 8 show a fourth modification of the ablation therapeutic treatment section 62.

In the first to fourth modifications, the shape of the therapeutic electrode 63 is the same as that of the therapeutic electrode 63 of the ablation therapeutic treatment section 62 of the resectoscope 1 of the first embodiment. Specifically, the bend angle α1 of the bend portion 63b of the therapeutic electrode 63 in the first modification, the bend angle α2 of the bend portion 63b of the therapeutic electrode 63 in the second modification, the bend angle α3 of the bend portion 63b of the therapeutic electrode 63 in the third modification and the bend angle α4 of the bend portion 63b of the therapeutic electrode 63 in the fourth modification are equal, and are set at, e.g. 45°. In addition, the length t1a of the bend portion 63b of the therapeutic electrode 63 in the direction of the perpendicular plane P1 in the first modification, the length t1b of the bend portion 63b of the therapeutic electrode 63 in the direction of the perpendicular plane P1 in the second modification, the length t1c of the bend portion 63b of the therapeutic electrode 63 in the direction of the perpendicular plane P1 in the third modification and the length t1d of the bend portion 63b of the therapeutic electrode 63 in the direction of the perpendicular plane P1 in the fourth modification are set to be equal.

In the first to fourth modifications, the shape of the compression section 64 is different. The shape of the compression section 64 in the third modification (see (A3) and (B3) in FIG. 8) is the same as that of the compression section 64 in the first embodiment. The bend angle β1 of the bend portion 64c of the compression section 64 in the first modification, the bend angle β2 of the bend portion 64c of the compression section 64 in the second modification and the bend angle β3 of the bend portion 64c of the compression section 64 in the third modification are equal and are set at, e.g. 45°. The bend angle β of the bend portion 64c of the compression section 64 in the fourth modification is 0°.

The length D2 of forward projection of the compression section 64 from the therapeutic electrode 63 in the second modification is greater than the length D3 of forward projection of the compression section 64 in the third modification (D3<D2). Further, the length D1 of forward projection of the compression section 64 from the therapeutic electrode 63 in the first modification is greater than the length D2 of forward projection of the compression section 64 in the second modification (D2<D1). Besides, the length t2a of the bend portion 64c of the compression section 64 in the direction of the perpendicular plane P2 in the first modification, the length t2b of the bend portion 64c of the compression section 64 in the direction of the perpendicular plane P2 in the second modification, the length t2c of the bend portion 64c of the compression section 64 in the direction of the perpendicular plane P2 in the third modification and the length t2d of the bend portion 64c of the compression section 64 in the direction of the perpendicular plane P2 in the fourth modification are set to establish the following relationships:

t2a>t2b>t2c>t2d, and t2d=0.

Figure 9A:
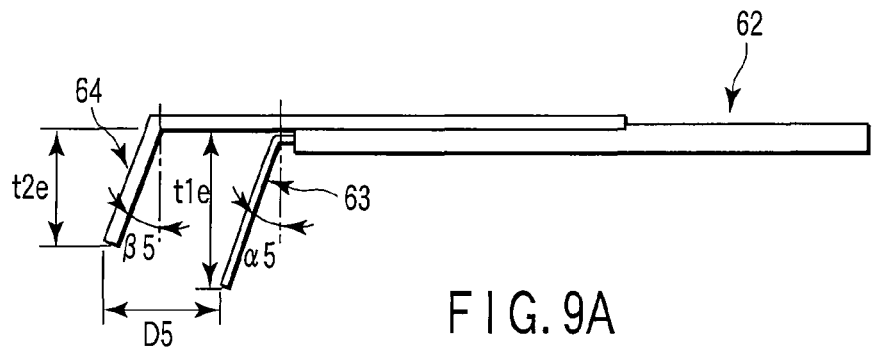
FIG. 9A is a side view showing an ablation therapeutic treatment section according to a fifth modification of the resectoscope of the first embodiment.
Figure 9B:
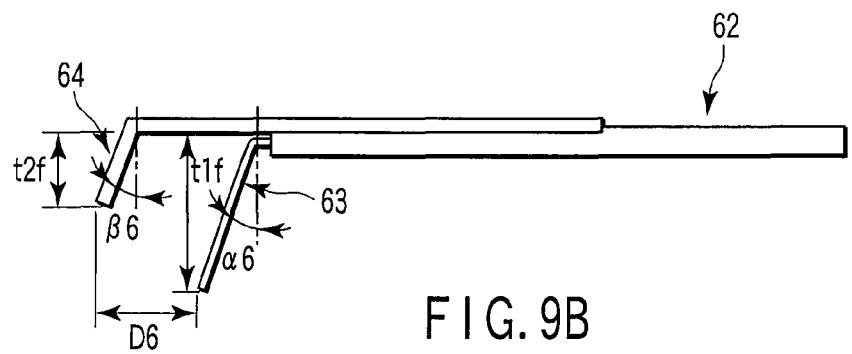
FIG. 9B is a side view showing an ablation therapeutic treatment section according to a sixth modification of the resectoscope of the first embodiment.
Figure 9C:
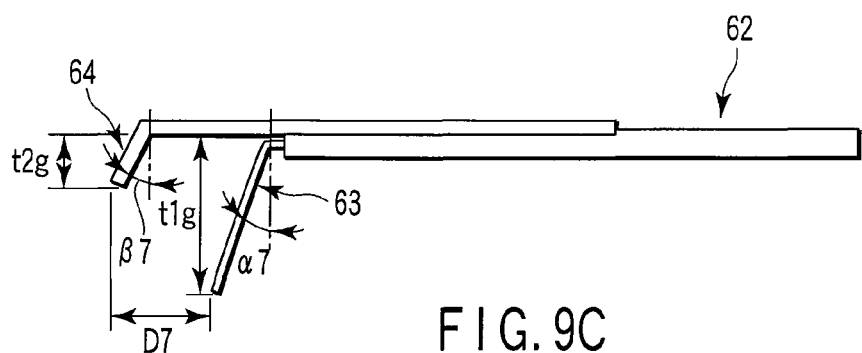
FIG. 9C is a side view showing an ablation therapeutic treatment section according to a seventh modification of the resectoscope of the first embodiment.
Figure 9D:
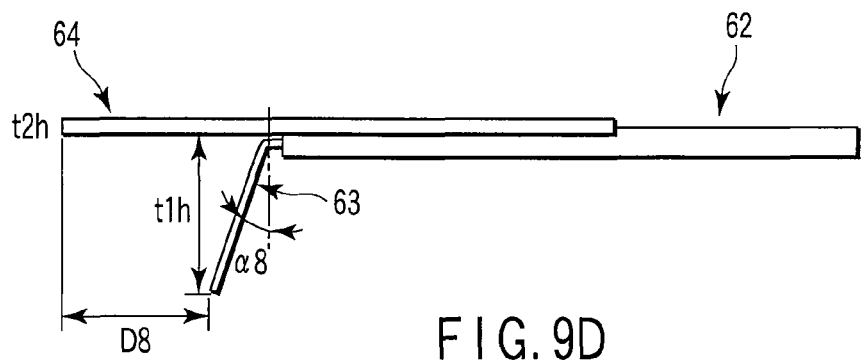
FIG. 9D is a side view showing an ablation therapeutic treatment section according to an eighth modification of the resectoscope of the first embodiment.

FIG. 9A shows a fifth modification of the ablation therapeutic treatment section 62 of the resectoscope 1 of the first embodiment, FIG. 9B shows a sixth modification of the ablation therapeutic treatment section 62 of the resectoscope 1 of the first embodiment, FIG. 9C shows a seventh modification of the ablation therapeutic treatment section 62 of the resectoscope 1 of the first embodiment, and FIG. 9D shows an eighth modification of the ablation therapeutic treatment section 62 of the resectoscope 1 of the first embodiment.

In the fifth to eighth modifications, the shape of the therapeutic electrode 63 and the shape of the compression section 64 are different from those of the ablation therapeutic treatment section 62 of the resectoscope 1 of the first embodiment. Specifically, the bend angle α5 of the bend portion 63b of the therapeutic electrode 63 in the fifth modification, the bend angle α6 of the bend portion 63b of the therapeutic electrode 63 in the sixth modification, the bend angle α7 of the bend portion 63b of the therapeutic electrode 63 in the seventh modification and the bend angle α8 of the bend portion 63b of the therapeutic electrode 63 in the eighth modification are set at the same angle, e.g. 30°, which is less than the bend angle α of the bend portion 63b of the therapeutic electrode 63 in the first embodiment. Further, the length t1e of the bend portion 63b of the therapeutic electrode 63 in the direction of the perpendicular plane P1 in the fifth modification, the length t1f of the bend portion 63b of the therapeutic electrode 63 in the direction of the perpendicular plane P1 in the sixth modification, the length t1g of the bend portion 63b of the therapeutic electrode 63 in the direction of the perpendicular plane P1 in the seventh modification and the length t1h of the bend portion 63b of the therapeutic electrode 63 in the direction of the perpendicular plane P1 in the eighth modification are set to be equal.

In the fifth to eighth modifications, the shape of the compression section 64 is different. Specifically, the bend angle β5 of the bend portion 64c of the compression section 64 in the fifth modification, the bend angle β6 of the bend portion 64c of the compression section 64 in the sixth modification and the bend angle β7 of the bend portion 64c of the compression section 64 in the seventh modification are set at the same angle, e.g. 30°, which is less than the bend angle β of the bend portion 64c of the compression section 64 in the first embodiment. The bend angle β of the bend portion 64c of the compression section 64 in the eighth modification is 0°. Besides, the length t2e of the bend portion 64c of the compression section 64 in the direction of the perpendicular plane P2 in the fifth modification, the length t2f of the bend portion 64c of the compression section 64 in the direction of the perpendicular plane P2 in the sixth modification, the length t2g of the bend portion 64c of the compression section 64 in the direction of the perpendicular plane P2 in the seventh modification and the length t2h of the bend portion 64c of the compression section 64 in the direction of the perpendicular plane P2 in the eighth modification are set to establish the following relationships:

t2e>t2f>t2g>t2h, and t2h=0.

FIG. 10A and FIG. 10B show a ninth modification of the ablation therapeutic treatment section 62 of the resectoscope 1 of the first embodiment. In this modification, the bend angle α9 of the bend portion 63b of the therapeutic electrode 63 and the bend angle β9 of the bend portion 64c of the compression section 64 are set at different angles. The bend angle α9 of the bend portion 63b of the therapeutic electrode 63 is set at, e.g. 30° and the bend angle β9 of the bend portion 64c of the compression section 64 is set at, e.g. 45°.

With the first to ninth modifications, the same advantageous effects as in the first embodiment can be obtained.

Although not shown in the drawings, a coating such as a PTFE tube can be provided on the compression section 64 of each embodiment.

Where such a coating is provided, the embodiments enable smooth ablation of a living tissue without invasion of that living tissue.

The present invention is not limited to the above-described embodiments, and the invention can variously be modified without departing from the spirit of the invention.

An additional characteristic technical item of the present invention is described below.

Note (Item 1) An electrode for resection, which has a loop-shaped electrode at a distal end thereof, characterized in that a compression section having a loop shape, which is thicker than the loop-shaped electrode, is provided in front of the loop-shaped electrode, the compression section and the loop-shaped electrode are disposed in a forward direction relative to a perpendicular direction to a longitudinal direction, and the length of the compression section in the perpendicular direction is less than the length of the loop-shaped electrode in the perpendicular direction.

The present invention is effective in the field of an ablation therapeutic device which performs incision, resection, transpiration, etc. of a living body tissue, such as ablation of the prostate, by electrical resection under observation by an endoscope, the technical field of manufacturing and using a resectoscope in combination of this ablation therapeutic device, and the technical field of method of ablating a living body tissue.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for performing transurethral prostate resectioning using a device which is used in combination with a scope configured to observe a body cavity, the device comprising:
   a hollow insertion section which is configured to be inserted in the body cavity;
   a treatment portion which is configured to be inserted into the hollow insertion section; and
   an operation section which is configured to reciprocally move the treatment portion along a central axis of the hollow insertion section;
   wherein the treatment portion comprises:
   an active electrode section with a first loop-shaped portion at a distal end thereof, both ends of the first loop-shaped portion being respectively connected to the distal end portion thereof, and
   a detachment portion including a compression section with a second loop-shaped portion at a distal end thereof, both ends of the second loop-shaped portion being respectively connected to the distal end portion thereof;
   the method comprising the steps of:
   inserting the hollow insertion section into the body cavity leading to the prostate;
   inserting through the hollow insertion section the active electrode section operable with a high frequency current, and the compression section that is configured to contact the prostate and to detach the prostate;
   incising a part of the prostate with the active electrode section being pressed on the part of the prostate by applying the high-frequency current to the part of the prostate;
   ceasing the application of the high-frequency current to the part of the prostate after incising the part of the prostate;
   contacting the compression section with the incised portion of the prostate;
   pressing the compression section to the incised portion of the prostate, with the compression section being extended to a position in front of the active electrode section; and
   pushing out the compression section and detaching a detached portion including the incised portion of the prostate.

2. The method of claim 1, wherein if bleeding occurs during the detachment of the prostate, pressing the active electrode to a bleeding part of the detached portion of the prostate, and treating the bleeding part with the high-frequency current to stop bleeding of the bleeding part by coagulation.

3. The method of claim 1, wherein the step of detaching the detached portion of the prostate with the compression section is carried out while no high-frequency current is being applied to the prostate by the active electrode section.

4. The method of claim 1, wherein the active electrode section includes:
   a first lead extending along the central axis of the hollow insertion section and
   an active electrode having a first diameter wherein:
   the active electrode includes a first loop-shaped portion in front of a distal end portion of the first lead, and both ends of the first loop-shaped portion are respectively connected to the distal end portion of the first lead,
   the first loop-shaped portion of the active electrode is configured to acutely intersect a first imaginary plane perpendicular to a central axis of the hollow insertion section, and
   the active electrode further includes a first length which is a length of a segment between a first intersection intersecting the first lead, and a second intersection intersecting an axis parallel to the central axis of the hollow insertion section through a distal end of the first loop-shaped portion in the first imaginary plane perpendicular to the central axis of the hollow insertion section.

5. The method of claim 4, wherein the compression section includes:
   a second lead extending along the central axis of the hollow insertion section to the front of the first lead,
   a second loop-shaped portion in front of a distal end portion of the second lead, and both ends of the second loop-shaped portion being respectively connected to the distal end portion of the second lead,
   the second loop-shaped portion of the compression section is configured to acutely intersect a second imaginary plane perpendicular to the central axis of the hollow insertion section, and
   the compression section having a second diameter thicker than a first diameter.

6. The method according to claim 5, including a return electrode on the hollow insertion section.

7. The method according to claim 5, wherein an angle of the first loop-shaped portion and the plane perpendicular to the central axis of the hollow insertion section is substantially equal to an angle of the second loop-shaped portion and the plane perpendicular to the central axis of the hollow insertion section.

8. The method according to claim 7, wherein the angle is 45°.

9. The method according to claim 7, wherein the angle is 30°.

* * * * *